United States Patent [19]

Honma et al.

[11] Patent Number: 5,580,763

[45] Date of Patent: Dec. 3, 1996

[54] METHOD FOR FERMENTATION PRODUCTION OF XANTHAN GUM

[75] Inventors: Taira Honma, Jyoetsu; Shigehiro Nagura, Niigata-ken; Kanji Murofushi, Jyoetsu, all of Japan

[73] Assignees: Shin-Etsu Chemical Co., Ltd., Tokyo, Japan; Shin-Etsu Bio, Inc., San Diego, Calif.

[21] Appl. No.: 296,115

[22] Filed: Aug. 25, 1994

[30] Foreign Application Priority Data

Nov. 8, 1993 [JP] Japan ........................... 5-277997

[51] Int. Cl.$^6$ ........................................ C12P 19/06
[52] U.S. Cl. ............................... 435/104; 536/114
[58] Field of Search .......................... 435/104; 536/114

[56] References Cited

U.S. PATENT DOCUMENTS

| 4,326,053 | 4/1982 | Kang et al. ........................ 435/243 |
| 4,374,929 | 2/1983 | Weisrock et al. ..................... 435/104 |
| 4,692,408 | 9/1987 | Banks et al. ........................ 435/104 |

FOREIGN PATENT DOCUMENTS

| 58-165798 | 9/1983 | Japan . |
| 60-058089 | 4/1985 | Japan . |
| 61-092591 | 5/1986 | Japan . |
| 61-173796 | 8/1986 | Japan . |
| 61-173795 | 8/1986 | Japan . |
| 2009385 | 1/1990 | Japan . |
| 2218701 | 8/1990 | Japan . |
| 2012792 | 8/1979 | United Kingdom . |

*Primary Examiner*—Herbert J. Lilling
*Attorney, Agent, or Firm*—McAulay Fisher Nissen Goldberg & Kiel, LLP

[57] ABSTRACT

A method for the fermentation production of xanthan gum which comprises the step of carrying out culture by using a water-soluble inorganic nitrogen component alone as the nitrogen source of a production medium, and by mixing and using the water-soluble inorganic nitrogen component and a water-insoluble organic nitrogen component as the nitrogen sources of a seed fermentation medium.

5 Claims, 1 Drawing Sheet

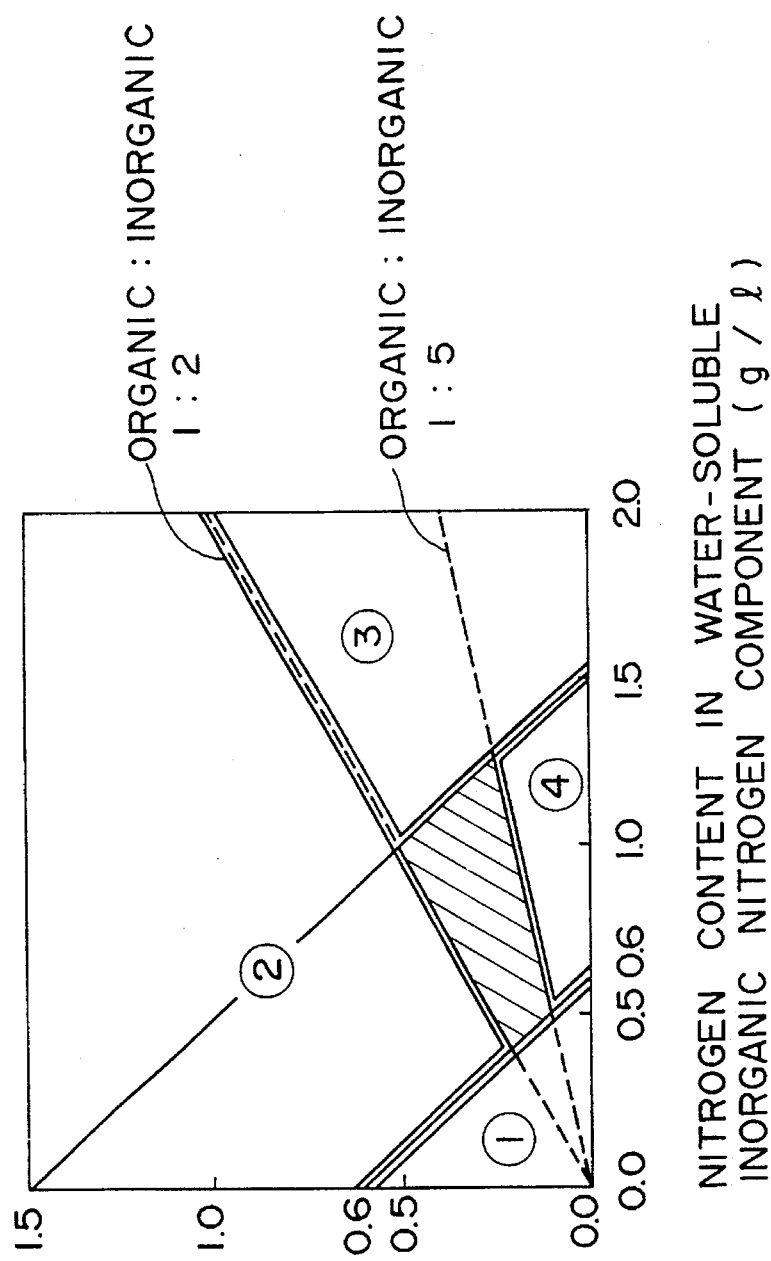

METHOD FOR FERMENTATION PRODUCTION OF XANTHAN GUM

1. FIELD OF THE INVENTION

The present invention relates to a method for the production of xanthan gum by fermentation. More specifically, the present invention relates to a method for producing xanthan gum with improved efficiency and quality.

2. BACKGROUND OF THE INVENTION

Water-soluble viscous polysaccharides, such as, gum arabic, xanthan gum, guar gum and rhamsan gum, have been widely utilized in the food, paint, paper making, cosmetic, medicine, petroleum recovery and similar industries. In recent years, the demand for such polysaccharides has increased, particularly for the most widely used, xanthan gum. Xanthan gum exhibits excellent characteristics, such as, a thickening function, an emulsion stabilizing effect, salt resistance, pH resistance and stability to various enzymes, which has led to increased usage of xanthan gum as an additive.

Xanthan gum may be obtained by aerobically culturing microorganisms of the Xanthomonas genus, for example, *X. campestris* in an aqueous culture medium having a pH of from 5.5 to 9 and containing at least one carbon source, e.g., glucose, molasses and starch, and the like, a water-soluble nitrogen source, such as, peptone or yeast extract, a magnesium salt, phosphate ions and other trace components. In general, after the cultivation, the culture medium is sterilized, and the desired component is precipitated with an alcohol, such as, ethanol or isopropanol and then dried. Preparative methods of the xanthan gum are described in U.S. Pat. Nos. 3,020,206, 3,251,479, 3,391,060, 3,433,708, 3,594,280, 4,282,321 and 8,659,026.

In addition to *X. campestris*, other known Xanthomonas bacteria can be used to produce xanthan gum, such as, *X. carotate, X. incanae, X. begoniae, X. paravericola, X. translucens, X. vasculorum* and *X. hederae.*

The usual procedure for carrying out such fermentations involves two separate steps. First, the organism to be used is subjected to a relatively small scale culturing step to build up the number or concentration of bacteria. This is usually referred to herein as the seed fermentation or seed culturing step. Thereafter, a portion of this seed culture having a relatively high concentration of bacteria is inoculated into a larger scale vessel containing an appropriate medium for the actual production of xanthan, referred to herein as the production culture or fermentation. Correspondingly, the medium for the seed culture is referred to as the seed culture medium and that for the production culture is referred to as the production culture medium.

It is conventional to purify the fermentation broth containing the xanthan gum product by the use of centrifugal separation or cake filtration to remove undissolved substances such as, bacteria residue and water insoluble unconsumed nitrogen components therein. However, the employment of the centrifugal separation or cake filtration is not practical from the viewpoints of cost and operation, because the fermentation liquid is highly viscous and thus a dilution step using water and a subsequent concentration step are required.

Other purification techniques are known in which the undissolved substances in the fermentation liquid are solubilized by an enzyme treatment. For example, U.S. application Ser. No. 07/990,758 discloses a clarifying process which comprises a continuous treatment with alkaline protease and lysozyme. U.S. Pat. Nos. 3,966,618 and 4,010,071 disclose clarifying methods using an alkaline and neutral protease. E.P. Pat. No. 78,621 has suggested a method using an acidic protease and a neutral protease, and U.S. Pat. No. 4,119,491 has suggested a technique in which after a protease treatment, an aqueous polymer solution is brought into contact with a silicate solid to remove cells from the aqueous polymer solution. Also disclosed are techniques using other materials with protease, for example, an enzyme treatment using polysaccharase and protease in U.S. Pat. No. 4,431,734, a method using an enzyme having a polygalacturonase activity and an enzyme having a protease activity in U.S. Pat. No. 4,904,568, and a method using a composite enzyme having β-1,3-glucanase activity and protease activity in E.P. 39,962. Also known are purification techniques using other enzymes including a method using an enzyme with a nuclease activity and a purification method using cellulase as suggested in U.S. Pat. No. 4,729,958 and U.S. Pat. No. 4,416,990, respectively. In all of these methods using enzyme treatments, troublesome steps, such as, dilution and concentration as required by the conventional filtration and centrifugal separation purification techniques can be omitted. Thus, these enzymatic purification methods are advantageous from economical and operational viewpoints.

Nitrogen sources which are used for both the seed culture and the production culture may be either water-insoluble or water soluble. Water-insoluble organic nitrogen sources which can be used in the culture medium include meals, such as, distillation dregs disclosed in U.S. Pat. No. 3,000,790, soybean meal disclosed in U.S. Pat. No. 3,335,447, U.K. Patent Nos. 2,012,792 A and 8,115,854, and corn meal described in U.S. Pat. Nos. 3,271,267 and 3,455,786.

Water-soluble inorganic nitrogen sources include ammonium salts, such as, ammonium nitrate, ammonium bromate, ammonium lactate, ammonium hydrochloride, ammonium phosphate, ammonium acetate, ammonium sulfate and urea, which are described in U.S. Pat. Nos. 3,391,060, 4,245,046, 4,282,321 and 4,394,447, U.K. Patent Nos. 2,012,792 and 8,115,855, French Patent No. 7,605,933, E.P. Patent No. 66,961 and Japanese Patent Application Laid-open Nos. 165,798/1983, 92,591/1986, 173,796/1986 and 9,385/1990.

When an undissolved water-insoluble organic substance, such as, a meal, is utilized as the sole nitrogen source, the growth ratio of the bacteria during the seed fermentation culture and the fermentation productivity of the xanthan gum during the production culture are high, and the xanthan gum product exhibits good viscosity effects in aqueous solution. However, the fermentation broth at the end of the fermentation contains about 5 to 10 g/l of the unconsumed water-insoluble nitrogen component, the cellular residue of the bacteria and the like, in addition to about 20 to 50 g/l of the xanthan gum product. In order to produce xanthan gum having high transparency, it is necessary to remove the water-insoluble component derived from the culture medium and the cellular residue of the bacteria. However, even if a lytic enzyme treatment with protease, lysozyme or the like is utilized, the aqueous solution of xanthan gum and the xanthan gum product which is separated and/or extracted from the fermentation liquid exhibits poor transparency.

On the other hand, if a water-soluble inorganic nitrogen source is used for both the seed culture and production culture medium, the bacterial growth lags during both the seed fermentation culture and the production culture. As a result, the productivity and the final production level of xanthan gum in the production culture is undesirably low, e.g., 10 g/l or less. As used herein, the term "productivity" means the amount of xanthan gum produced per hour.

If a water-insoluble organic nitrogen component is used in the seed fermentation medium and a water-soluble inorganic nitrogen component is used in the production medium, the fermentation liquid at the end of the fermentation contains about 3 to 6 g/l of undissolved substances composed of bacterial residue, water-insoluble unconsumed nitrogen component and the like. Therefore, even if an enzyme treatment is used for purification, the aqueous xanthan gum solution obtained and the xanthan product therefrom are not sufficiently transparent.

When a water-soluble inorganic nitrogen component is used in the seed fermentation medium and a water-insoluble organic nitrogen component is used as the nitrogen source in the production medium, the growth rate of the bacteria in the seed fermentation medium is low, so that the bacterial growth in the production culture also lags. As a result, the productivity of the xanthan gum deteriorates. In addition, the fermentation liquid at the end of the fermentation contains about 4 to 8 g/l of undissolved substances composed of bacterial residue, the water-insoluble unconsumed nitrogen component and the like, and consequently, sufficient purification cannot be achieved with a lytic enzyme treatment.

Additional nitrogen sources include aqueous organic nitrogen components of biological extracts, such as, yeast extract, peptone, bouillon, tryputon, malt extract, enzyme-degraded casein, gelatin and soybean whey as well as protein amino acids, such as, glutamic acid, aspartic acid, alanine, proline and threonine, which have been described in U.S. Pat. Nos. 3,427,226, 3,433,708, 3,391,060, 4,119,546, 4,263,399 and 4,375,512, Japanese Patent Publication No. 42,634/1980, Japanese Patent Application Laid-open Nos. 165,798/1983, 58,089/1985, 92,591/1986, 173,795/1986, 86,894/1989 and 218,701/1990. They do not contain any water-insoluble component and consequently, can be used to prepare xanthan gum having excellent transparency. However, they are not practical because of their cost.

The compositions of the conventional culture media which have been described above and their characteristics are set forth in Table 1 (I), (II), and (III),

TABLE 1 (I)

Compositions of Conventional Culture Medium in Fermentation Production of Xanthan Gum

| Combination | Nitrogen Component in Seed Fermentation Medium | Nitrogen Component in Production Medium |
| --- | --- | --- |
| 1 | Insoluble & organic | Insoluble & organic |
| 2 | Insoluble & organic | Water-soluble & inorganic |
| 3 | Insoluble & organic | Water-soluble & organic |
| 4 | Water-soluble & inorganic | Insoluble & organic |
| 5 | Water-soluble & inorganic | Water-soluble & inorganic |
| 6 | Water-soluble & inorganic | Water-soluble & organic |
| 7 | Water-soluble & organic | Insoluble & organic |
| 8 | Water-soluble & organic | Water-soluble & inorganic |
| 9 | Water-soluble & organic | Water-soluble & organic |

TABLE 1 (II)

| Combination | Growth Ratio of Bacteria in Seed Fermentation Medium | Productivity of XG in Production Medium | Undissolved Substances in Production Medium |
| --- | --- | --- | --- |
| 1 | Δ | o | Many |
| 2 | Δ | Δ | Many |
| 3 | Δ | o | Many |
| 4 | x | Δ | Many |
| 5 | x | x | Few |
| 6 | x | x | Few |
| 7 | o | o | Many |
| 8 | o | Δ | Few |
| 9 | o | o | Few | o : Good, Δ: Medial, and x: Bad.

TABLE 1 (III)

| Combination | Effect of Enzyme Treatment | Expression Properties of Viscosity | Cost of Culture Medium |
| --- | --- | --- | --- |
| 1 | x | o | o |
| 2 | x | o | o |
| 3 | x | o | x |
| 4 | x | Δ | o |
| 5 | o | x | Δ |
| 6 | o | Δ | x |
| 7 | x | o | x |
| 8 | o | Δ | x |
| 9 | o | o | x | o : Good, Δ: Medial, and x: Bad.

As shown, none of the conventional fermentation techniques, and combinations of a culture medium compositions provide satisfactory productivity levels, purification and transparency levels of the enzyme treatment, viscosity effects, under desirable economical conditions.

SUMMARY OF THE INVENTION

It is an object of the present invention to provide a method for the production of xanthan gum at high productivity levels and produces xanthan gum having good transparency, high purity, and which exhibits an excellent viscosity effect on aqueous solutions thereof.

It is another object of the invention to provide a process which produces the above high quality xanthan gum under satisfactory economic conditions.

It is yet another object of the invention to provide a high quality xanthan gum having good transparency, high purity, and which exhibits an excellent viscosity effect on aqueous solutions thereof.

We have discovered that these and as well as other objects are achieved by the steps of:

1. preparing a seed fermentation culture in a medium containing as a nitrogen source, a combination of a water-soluble inorganic nitrogen component and a water-insoluble organic nitrogen component;

2. inoculating an aliquot of the seed culture into a production culture medium containing as the sole nitrogen source, a water-soluble inorganic nitrogen component;

3. carrying out the production culturing or fermentation under conventional conditions, and thereafter, subjecting the fermentation broth obtained to clarification using conventional enzyme treatments as described hereinabove, and then precipitating the xanthan gum, usually with alcohol, e.g., ethanol or isopropanol, followed by drying to obtain the desired purified xanthan gum product.

With the inventive procedure, improved growth rate of the bacteria in the seed fermentation culture is obtained which results in acceleration of the bacterial growth in the production culture. This produces substantial improvements in the productivity of the xanthan gum. In addition, since the amount of the water-insoluble organic nitrogen component contained in the culture medium is reduced, the efficiency and effects of the subsequent enzyme treatment are improved.

With the inventive process, high productivity of xanthan gum can be obtained using inexpensive culture medium components, providing decreased cost for the manufacturing process and resulting xanthan gum product. In addition, the transparency of the aqueous product solution can easily be improved to desired levels merely by treating the fermentation liquid with an enzyme having a lytic activity, such as, a protease or lysozyme. Thus, the more costly and intricate conventional purification steps, such as, dilution, filtration and concentration can be omitted. We have also discovered that the xanthan gum obtained with the present invention not only exhibits improved transparency, it exhibits excellent ability to effect (usually increase) the viscosity of solutions to which it is added. The inventive product thus finds broad use in many expanded industrial fields.

BRIEF DESCRIPTION OF THE DRAWING

FIG. 1 is a graph showing a mixing ratio of a water-soluble inorganic nitrogen component to a water-insoluble organic component in a seed fermentation medium.

DETAILED DESCRIPTION OF PREFERRED EMBODIMENTS

As xanthan gum producing bacteria suitable for the practice of the present invention, the conventional Xanthomonas bacteria (bacteria in a Xanthomonas genus) which are available as public deposits at well known depositories, such as the American Type Culture Collection and the NRRL, may be used. In addition to the above-mentioned *X. campestris*, for example, *X. carotate, X. incanae, X. begoniae, X. paravericola, X. translucens, X. vasculorum* and *X. hederae* can be used to produce the xanthan gum. Preferred strains are the publicly available *X. campestris* deposited with the number of ATCC 55298, ATCC 55258 and NRRL B-1459.

A wide variety of water-soluble inorganic nitrogen components can be used for the inventive method. Preferred are ammonium salts, such as, ammonium nitrate, ammonium bromate, ammonium lactate, ammonium hydrochloride, ammonium phosphate, ammonium acetate, ammonium sulfate and urea. Ammonium nitrate having a high nitrogen content is particularly preferable, however, there is no particular limitation on the specific water-soluble nitrogen component.

Similarly, a wide variety of water-insoluble organic nitrogen components can be used in the method of the present invention. These include grain-processed products, such as, soybean meal, peanut meal, corn extract and cotton seed extract. Particularly preferred is soybean meal having a high nitrogen content. However, here again, there is no particular limitation as to the specific water-insoluble organic nitrogen component used.

We have further discovered that by controlling the total amount of nitrogen in each of the seed and production cultures and also, controlling the ratio of nitrogen content attributable from the water soluble inorganic nitrogen source and the water insoluble organic nitrogen source, respectively, the bacterial growth during the seed culture can be maximized, the xanthan production in the production culture can be maximized, the efficiency of the enzyme clarification step can be improved and the overall cost of the process can be reduced. It is noted that in referring to the nitrogen content and/or ratio of nitrogen contents for either the seed fermentation medium or production fermentation medium, the content and/or ratio is always that at at the commencement of the seed culturing step or production culturing step.

In particular, we have discovered that the best results are obtained when, at the commencement of the seed fermentation step, the ratio of the nitrogen contents of the water-insoluble organic nitrogen component and the water-soluble inorganic nitrogen component which are added as the nitrogen sources for the seed fermentation medium is between about 1:2 to 1:5, and the total nitrogen content in the seed fermentation medium is in the range of from about 0.6 to 1.5 g/l (hatched region in FIG. 1).

If the total nitrogen content in the seed fermentation medium is less than about 0.6 g/l [region (1) in FIG. 1], the absolute amount of the nitrogen content is low, so that the growth ratio of the bacteria can be undesirably low. The nitrogen contents of the respective nitrogen components disclosed in U.K. Patent No. 2,012,792A referred to above are within this region.

If the ratio of the nitrogen content in the water-soluble inorganic nitrogen component to that in the water-insoluble organic nitrogen component is less than about 2 and if the total nitrogen content in the seed fermentation medium is more than 0.6 g/l [region (2) in FIG. 1], the amount of water-insoluble organic nitrogen component is excessive, and this can adversely effect enzyme purification carried out after completion of the production culture.

If the ratio of the nitrogen content in the water-soluble inorganic nitrogen component to that in the water-insoluble organic nitrogen component is more than about 2 and if the total nitrogen content in the seed fermentation medium is more than about 1.5 g/l [region (3) in FIG. 1], the absolute amount of the nitrogen component in the seed fermentation culture is large, but the growth ratio of the bacteria is relatively low and the cost for medium is high. Furthermore, in this case, since the amount of undissolved bacterial residue, unconsumed nitrogen component and the like increase, the purification effect by the enzyme may be insufficient.

If the ratio of the nitrogen content in the water-soluble inorganic nitrogen component to that of the water-insoluble organic nitrogen component is more than about 5 and if the total nitrogen content in the seed fermentation medium is in the range of from about 0.6 to 1.5 g/l [a region (4) in FIG. 1], the water-insoluble organic nitrogen content is low and the growth ratio of the bacteria can be undesirably low.

The nitrogen content of the water-soluble inorganic nitrogen component used as the nitrogen source for the production medium at the commencement of the production step in the inventive method is in the range of from about 0.2 to 1.0 g/l, preferably from about 0.3 to 0.6 g/l. If the nitrogen content of the water soluble inorganic nitrogen component is less than about 0.2 g/l, the productivity of the xanthan gum is not significantly improved. If the nitrogen content of the water-soluble inorganic nitrogen component is more than 1.0 g/l, the cellular residue of the production bacteria increases, so that the enzyme purification effect after completion of the fermentation is insufficient.

In carrying out the method of the present invention, the amount of the seed fermentation medium inoculated into the production medium is in the range of from about 5 to 15% by volume. If the amount of the seed fermentation medium to be inoculated is less than about 5%, the initial amount of the bacteria in the production medium is low, the growth of the bacteria lags, and consequently, the productivity of the xanthan gum tends to undesirably decline. If it is more than about 15%, the cost of the culture medium increases, and the water-insoluble substances derived from the seed fermentation medium also increase, which can undesirably effect the enzyme purification.

In the method of the present invention, in addition to the nitrogen source, conventional culture medium components, such as, a carbon source, phosphate, magnesium salt and trace components which are necessary to ferment the xanthan gum production bacteria are used.

Examples of the carbon source include saccharoses, such as, glucose, sucrose, xylose, molasses, starch, maltose and dextrin as well as polyvalent alcohols, such as, glycerin and sorbitol. They can be used alone or in combination. The amount of the carbon source to be added is in the range of from about 5 to 70 g/l.

Examples of the phosphate include potassium primary phosphate, potassium secondary phosphate, sodium primary phosphate and sodium secondary phosphate. These can be used alone or in combination. The amount of the phosphate to be added is in the range of from 1 to 5 g/l.

Examples of the magnesium salt include magnesium phosphate, magnesium sulfate and magnesium nitrate, and they can be used alone or in combination. The amount of the magnesium salt to be added is in the range of from about 0.1 to 1 g/l.

Examples of the trace components include ferrous chloride, ferric chloride, ferrous nitrate, ferric nitrate, ferrous phosphate, ferric phosphate, zinc sulfate, zinc chloride, zinc nitrate and zinc phosphate, and these can be used alone or in combination. The amount of the trace components to be added is in the range of from about 0.02 to 0.08 g/l.

In the present invention, a variety of lytic enzymes may be used for the purification step. Examples of the preferable lytic enzymes for treating the fermented xanthan gum culture medium include alkaline protease, neutral protease, acidic protease and lysozyme. Of these, alkaline protease and lysozyme are particularly preferred.

The following examples illustrate the present invention.

EXAMPLE 1

Composition A: Seed fermentation medium components:
 Glucose: 5 g/l
 $NH_4NO_3$: 2.1 g/l
 (nitrogen content: 0.74 g/l)
 Defatted soybean meal: 5.4 g/l
 (nitrogen content: 0.35 g/l)
 Ratio=0.35/0.74=0.47
 NaCl: 9 g/l
 Water: 0.3 l
Composition B: Production medium components:
 Glucose: 50 g/l
 $NH_4NO_3$: 0.9 g/l
 (nitrogen content: 0.32 g/l)
 $KH_2PO_4$: 2 g/l
 $MgSO_4 \cdot 7H_2O$: 0.5 g/l
 Trace components: 0.05 g/l
 Water: 2.7 l A 2 ml sample of bacteria (concentration=$10^{10}$/ml) [*Xanthomonas campestris* (ATCC 55298)] were inoculated into a culture medium comprising the above-mentioned Composition A, and culturing in shake flask (shake culturing) was carried out for 24 hours. Afterward, this culture medium was added to a culture medium comprising the above-mentioned composition B in a 5-liter fermenter, and aeration culturing was then carried out at 30° C. at a pH 6.5–7.0 for 2 days. Next, the resulting fermentation liquid was subjected to an enzyme treatment with alkaline protease and lysozyme in accordance with a procedure described in Japanese Patent Application No. 54898/1992.

Specifically, the fermentation liquid was heat treated at a temperature of 55° C. at an initial pH 11 for 90 minutes with stirring, and afterward the pH of the fermentation liquid was adjusted to 8.5, while maintaining the temperature at 55° C. by the dropwise addition of 26 wt. % NaOH solution. An aqueous suspension containing 300 ppm of alkaline protease (trade name Bioprase; made by Nagase Biochemical Co., Ltd.) was filtered through a 0.4 µm microfilter. The resulting filtrate was added to the above pH-adjusted fermentation liquid, and the solution was then treated at 55° C. for 2 hours with stirring.

Next, the fermentation liquid was cooled to 35° C., and the pH of the solution was adjusted to 6.5 by dropwise addition of a 10 wt. % $H_2SO_4$ solution. Afterward, 3 ppm of lysozyme (trade name Lysozyme Taiyo; made by Taiyo Chemical Co., Ltd.) were added to the pH-adjusted solution and the solution was stirred at 35° C. for 1 hour.

EXAMPLE 2

Composition A: Seed fermentation medium components:
 Glucose: 5 g/l
 $NH_4NO_3$: 2.5 g/l
 (nitrogen content: 0.88 g/l)
 Defatted soybean meal: 3.4 g/l
 (nitrogen content: 0.22 g/l)
 Ratio=0.22/0.88=0.25
 NaCl: 9 g/l
 Water: 0.3 l
Composition B: Production medium components:
 Glucose: 50 g/l
 $NH_4NO_3$: 0.9 g/l
 (nitrogen content: 0.32 g/l)
 $KH_2PO_4$: 2 g/l
 $MgSO_4 \cdot 7H_2O$: 0.5 g/l
 Trace components: 0.05 g/l
 Water: 2.7 l Fermentation was carried out in the culture media comprising the above-mentioned compositions A and B by the same procedure as in Example 1, and the same enzyme treatment as in Example 1 was used.

EXAMPLE 3

Composition A: Seed fermentation medium components:
 Glucose: 5 g/l
 $NH_4NO_3$: 2.5 g/l
 (nitrogen content: 0.88 g/l)
 Defatted soybean meal: 3.4 g/l
 (nitrogen content: 0.22 g/l)
 Ratio=0.22/0.88=0.25
 NaCl: 9 g/l
 water: 0.3 l
Composition B: Production medium components:
 Glucose: 50 g/l
 $NH_4NO_3$: 7 g/l
 (nitrogen content: 0.60 g/l)
 $KH_2PO_4$: 2 g/l MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

EXAMPLE 4

Composition A: Seed fermentation components:
  Glucose: 5 g/l
  NH$_4$NO$_3$: 2.5 g/l
  (nitrogen content: 0.88 g/l)
  Defatted soybean meal: 3.4 g/l
  (nitrogen content: 0.22 g/l)
  Ratio=0.22/0.88=0.25
  NaCl: 9 g/l
  Water: 0.3 l
Composition B: Production medium components:
  Glucose: 50 g/l
  NH$_4$NO$_3$: 2.8 g/l
  (nitrogen content: 0.98 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

EXAMPLE 5

Composition A: Seed fermentation medium components:
  Glucose: 5 g/l
  NH$_4$NO$_3$: 1.3 g/l
  (nitrogen content: 0.46 g/l)
  Defatted soybean meal: 3.4 g/l
  (nitrogen content: 0.22 g/l)
  Ratio=0.22/0.46=0.48
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

EXAMPLE 6

Composition A: Seed fermentation medium components:
  Glucose: 5 g/l
  NH$_4$NO$_3$: 1.5 g/l
  (nitrogen content: 0.53 g/l)
  Defatted soybean meal: 1.7 g/l
  (nitrogen content: 0.11 g/l)
  Ratio=0.11/0.53=0.21
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

EXAMPLE 7

Composition A: Seed fermentation medium components:
  Glucose: 5 g/l
  NH$_4$NO$_3$: 2.7 g/l
  (nitrogen content: 0.95 g/l)
  Defatted soybean meal: 6.3 g/l
  (nitrogen content: 0.41 g/l)
  Ratio=0.41/0.95=0.43
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

EXAMPLE 8

Composition A: Seed fermentation medium components:
  Glucose: 5 g/l
  NH$_4$NO$_3$: 3.2 g/l
  (nitrogen content: 1.12 g/l)
  Defatted soybean meal: 3.7 g/l
  (nitrogen content: 0.24 g/l)
  Ratio=0.24/1.12=0.21
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

COMPARATIVE EXAMPLE 1

Composition A: Seed fermentation medium components:
  Glucose: 5 g/l
  NH$_4$NO$_3$: 3.1 g/l
  (nitrogen content: 1.09 g/l)
  NaCl: 9 g/l
  Water: 0.3 l Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions by the same procedure as in Example 1, and the same enzyme treatment as in Example 1 was used.

COMPARATIVE EXAMPLE 2

Composition A: Seed fermentation medium components:
  Glucose: 5 g/l
  Defatted soybean meal: 17 g/l
  (nitrogen content: 1.11 g/l)
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions by the same procedure as in Example 1, and the same enzyme treatment as in Example 1 was used.

COMPARATIVE EXAMPLE 3

Composition A: Seed fermentation medium components:
  Glucose: 5 g/l
  NH$_4$NO$_3$: 3.1 g/l
  (nitrogen content: 1.09 g/l)
  NaCl: 9 g/l
  Water: 0.3 l
Composition B: Production medium components:
  Glucose: 50 g/l
  Defatted soybean meal: 4.6 g/l
  (nitrogen content: 0.30 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions by the same procedure as in Example 1, and the same enzyme treatment as in Example 1 was used.

COMPARATIVE EXAMPLE 4

Composition A: Seed fermentation medium components:
  Glucose: 5 g/l
  Defatted soybean meal: 17 g/l
  (nitrogen content: 1.11 g/l)
  NaCl: 9 g/l
  Water: 0.3 l
Composition B: Production medium components:
  Glucose: 50 g/l
  Defatted soybean meal: 4.6 g/l
  (nitrogen content: 0.30 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions by the same procedure as in Example 1, and the same enzyme treatment as in Example 1 was used.

COMPARATIVE EXAMPLE 5

Composition A: Seed fermentation medium components:
  Glucose: 5 g/l
  NH$_4$NO$_3$: 3.1 g/l
  (nitrogen content: 1.09 g/l)
  NaCl: 9 g/l
  Water: 0.3 l
Composition B: Production medium components:
  Glucose: 50 g/l
  NH$_4$NO$_3$: 0.8 g/l
  (nitrogen content: 0.28 g/l)
  Defatted soybean meal: 0.3 g/l
  (nitrogen content: 0.02 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions by the same procedure as in Example 1, and the same enzyme treatment as in Example 1 was used.

COMPARATIVE EXAMPLE 6

Composition A: Seed fermentation medium components:
  Glucose: 5 g/l
  NH$_4$NO$_3$: 1.0 g/l
  (nitrogen content: 0.35 g/l)
  Defatted soybean meal: 3.4 g/l
  (nitrogen content: 0.22 g/l)
  Ratio=0.22/0.35=0.63
  NaCl: 9 g/l
  Water: 0.3 l
Composition B: Production medium components:
  Glucose: 50 g/l
  NH$_4$NO$_3$: 0.9 g/l
  (nitrogen content: 0.32 g/l)
  KH$_2$PO$_4$: 2 g/l
  MgSO$_4$.7H$_2$O: 0.5 g/l
  Trace components: 0.05 g/l
  Water: 2.7 l Fermentation was carried out in the culture media comprising the above-mentioned compositions A and B by the same procedure as in Example 1, and the same enzyme treatment as in Example 1 was used.

COMPARATIVE EXAMPLE 7

Composition A: Seed fermentation medium components:
  Glucose: 5 g/l
  NH$_4$NO$_3$: 2.0 g/l
  (nitrogen content: 0.70 g/l)
  Defatted soybean meal: 7.0 g/l
  (nitrogen content: 0.46 g/l)
  Ratio=0.46/0.70=0.66
  NaCl: 9 g/l
  Water: 0.3 l
Composition B: Production medium components:
  Glucose: 50 g/l NH$_4$NO$_3$: 0.9 g/l
(nitrogen content: 0.32 g/l)
KH$_2$PO$_4$: 2 g/l
MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

COMPARATIVE EXAMPLE 8

Composition A: Seed fermentation medium components:
Glucose: 5 g/l
NH$_4$NO$_3$: 3.5 g/l
(nitrogen content: 1.23 g/l)
Defatted soybean meal: 7.0 g/l
(nitrogen content: 0.46 g/l)
Ratio=0.46/1.23=0.37
NaCl: 9 g/l
Water: 0.3 l Composition B: Production medium components:
Glucose: 50 g/l
NH$_4$NO$_3$: 0.9 g/l
(nitrogen content: 0.32 g/l)
KH$_2$PO$_4$: 2 g/l
MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

COMPARATIVE EXAMPLE 9

Composition A: Seed fermentation medium components:
Glucose: 5 g/l
NH$_4$NO$_3$: 2.9 g/l
(nitrogen content: 0.32 g/l)
Defatted soybean meal: 2.7 g/l
(nitrogen content: 0.18 g/l)
Ratio=0.18/0.32=0.56
NaCl: 9 g/l
Water: 0.3 l Composition B: Production medium components:
Glucose: 50 g/l
NH$_4$NO$_3$: 0.9 g/l
(nitrogen content: 0.32 g/l)
KH$_2$PO$_4$: 2 g/l
MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

COMPARATIVE EXAMPLE 10

Composition A: Seed fermentation medium components:
Glucose: 5 g/l
NH$_4$NO$_3$: 2.5 g/l
(nitrogen content: 0.88 g/l)
Defatted soybean meal: 3.4 g/l
(nitrogen content: 0.22 g/l)
Ratio=0.22/0.88=0.25
NaCl: 9 g/l
Water: 0.3 l Composition B: Production medium components:
Glucose: 50 g/l
NH$_4$NO$_3$: 3.5 g/l
(nitrogen content: 1.23 g/l)
KH$_2$PO$_4$: 2 g/l
MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

COMPARATIVE EXAMPLE 11

Composition A: Seed fermentation medium components:
Glucose: 5 g/l
NH$_4$NO$_3$: 2.5 g/l
(nitrogen content: 0.88 g/l)
Defatted soybean meal: 3.4 g/l
(nitrogen content: 0.22 g/l)
Ratio=0.22/0.88=0.25
NaCl: 9 g/l
Water: 0.3 l Composition B: Production medium components:
Glucose: 50 g/l
NH$_4$NO$_3$: 0.4 g/l
(nitrogen content: 0.14 g/l)
KH$_2$PO$_4$: 2 g/l
MgSO$_4$.7H$_2$O: 0.5 g/l
Trace components: 0.05 g/l
Water: 2.7 l Fermentation was carried out in the culture media comprising the above-mentioned compositions A and B by the same procedure as in Example 1, and the same enzyme treatment as in Example 1 was used.

After completion of the enzyme treatment, each fermentation liquid was sampled, and xanthan gum was extracted and separated by the use of isopropanol in an amount of 1.5 times by weight of the sample weight. The separated product was then air-dried. Afterward, for each sample, the yield of the solid xanthan gum was measured. Furthermore, a 0.3% aqueous solution of the obtained solid xanthan gum was prepared, and the transmittancy and viscosity (Brookfield viscometer: 30 rpm) were then measured for each sample. The results are shown in Table 2.

The specific procedures used for these measurements are as follows:

1. Transparency (a) The transparency was measured using a spectrophotometer having a tungsten lamp for visible rays and a heavy hydrogen discharge tube for ultraviolet rays. A quartz cell 1 cm in layer length was used.

(b) Dry xanthan gum (0.90 g) was accurately measured into a 500 ml beaker containing 299.1 g of water. It was then dispersed to avoid air bubble incorporation and mixed by stirring for two hours until dissolved and air bubbles were removed. The temperature was adjusted to 20±0.5° C. The resulting solution was used as the test solution. The spectrophotometer light sources were 486.0 nm and 656.1 nm for the heavy hydrogen discharge tube. The test solution was introduced to a quartz cell and water was used as the reference. The permeability at 0% and 100% at a measured wavelength of 600 nm was adjusted. Thereafter, the test solution was put in a quartz cell of 10 cm so that the permeability of 600 nm could be read and measured.

2. Viscosity

The viscosity was measured using a Brookfield rotary viscometer with a No. 2 rotor and exchanger number of 10. For this measurement, a quantity corresponding to 0.9 g of dry xanthan gum was accurately measured into a 500 ml beaker containing 299.1 g of water. The mixture was stirred for two hours until it dissolved and air bubbles were removed. The temperature was adjusted to 25±0.5° C. This solution was used as the test solution. The viscosity test was carried out with the Brookfield rotary viscometer at a rotation of 60 rpm. After 30 seconds, the rotation was stopped and the measurement was read and multiplied by the exchange number.

TABLE 2

Results of Examples and Comparative Examples

| | Total Nitrogen Content | | | | | | Amount of bacteria in seed fermentation medium [g/l] | Amount of XG in production medium [g/l] | Undissolved substances in production medium [g/l] | 0.3% Aqueous XG solution | |
|---|---|---|---|---|---|---|---|---|---|---|---|
| | Seed fermentation medium | | | Production medium | | | | | | | |
| | $NH_4NO_3$ [g/l] | SF [g/l] | Total [g/l] | $NH_4NO_3$ [g/l] | SF [g/l] | Total [g/l] | | | | Transmittancy [%] | Viscosity [cP] |
| Examples | | | | | | | | | | | |
| 1 | 0.74 | 0.35 | 1.09 | 0.32 | — | 0.32 | 1.0 | 31 | 2.8 | 82 | 370 |
| 2 | 0.88 | 0.22 | 1.10 | 0.32 | — | 0.32 | 1.0 | 30 | 2.6 | 85 | 390 |
| 3 | 0.88 | 0.22 | 1.10 | 0.60 | — | 0.60 | 1.0 | 31 | 2.7 | 83 | 390 |
| 4 | 0.88 | 0.22 | 1.10 | 0.98 | — | 0.98 | 1.0 | 30 | 2.9 | 80 | 380 |
| 5 | 0.46 | 0.22 | 0.68 | 0.32 | — | 0.32 | 0.9 | 28 | 2.5 | 83 | 350 |
| 6 | 0.53 | 0.11 | 0.64 | 0.32 | — | 0.32 | 0.8 | 27 | 2.4 | 83 | 350 |
| 7 | 0.95 | 0.41 | 1.36 | 0.32 | — | 0.32 | 1.2 | 32 | 3.1 | 80 | 370 |
| 8 | 1.12 | 0.24 | 1.36 | 0.32 | — | 0.32 | 1.1 | 31 | 2.7 | 82 | 360 |
| Comparative Examples | | | | | | | | | | | |
| 1 | 1.09 | — | 1.09 | 0.32 | — | 0.32 | 0.3 | 8 | 1.5 | 88 | 240 |
| 2 | — | 1.11 | 1.11 | 0.32 | — | 0.32 | 0.7 | 24 | 4.8 | 56 | 370 |
| 3 | 1.09 | — | 1.09 | — | 0.30 | 0.30 | 0.3 | 23 | 6.7 | 37 | 380 |
| 4 | — | 1.11 | 1.11 | — | 0.30 | 0.30 | 0.7 | 33 | 3.4 | <10 | 360 |
| 5 | 1.09 | — | 1.09 | 0.28 | 0.02 | 0.30 | 0.2 | 21 | 2.2 | 80 | 340 |
| 6 | 0.35 | 0.22 | 0.55 | 0.32 | — | 0.32 | 0.7 | 25 | 2.3 | 82 | 310 |
| 7 | 0.70 | 0.46 | 1.16 | 0.32 | — | 0.32 | 1.2 | 31 | 3.4 | 74 | 370 |
| 8 | 1.23 | 0.46 | 1.69 | 0.32 | — | 0.32 | 1.3 | 32 | 3.5 | 72 | 380 |
| 9 | 1.02 | 0.18 | 1.20 | 0.32 | — | 0.32 | 0.5 | 24 | 2.0 | 81 | 300 |
| 10 | 0.88 | 0.22 | 1.10 | 1.23 | — | 1.23 | 1.0 | 32 | 3.3 | 76 | 350 |
| 11 | 0.88 | 0.22 | 1.10 | 0.14 | — | 0.14 | 1.0 | 16 | 1.8 | 81 | 270 |

As shown in the above examples and comparative example, with the present invention, an economical water-soluble inorganic nitrogen component and a water insoluble organic nitrogen component are mixed and used at a specific ratio (the former alone in a production culture) as nitrogen sources of a seed fermentation culture for mainly growing bacteria and the production culture for mainly producing the xanthan gum. This provides a high bacteria growth ratio in the seed fermentation culture and xanthan gum productivity in the production culture. In addition, when the resulting fermentation liquid is treated with a lytic enzyme and the solid xanthan gum is then extracted/separated from the fermentation liquid by the use of an organic solvent, a 0.3% by weight aqueous solution of this solid xanthan gum has a high transmittancy of 80% and excellent viscosity expression properties of 300 cP or more, in addition to excellent xanthan gum productivity.

What is claimed is:

1. In a method for the production of xanthan gum by the submerged fermentation of xanthan-producing microorganisms in a culture medium, wherein a seed culture step is first carried out in the presence of a seed culturing medium containing a first nitrogen source to increase the concentration of the microorganisms and produce a seed culture, a portion of the seed culture is then inoculated into a production culture medium containing a second nitrogen source and a product culture step is carried out to produce xanthan gum, the improvement which comprises the first nitrogen source comprising a combination of a water-insoluble nitrogen source and a water-soluble nitrogen source and the second nitrogen source consisting of water-soluble nitrogen source, wherein the ratio of the nitrogen contents of the insoluble nitrogen source to the soluble nitrogen source in the seed culture medium at the beginning of the seed culturing step is from 1:2 to 1:5, and the total nitrogen content in the seed medium is from 0.6 to 1.5 g/l.

2. The method of claim 1 wherein the total nitrogen content in the production medium is in the range from about 0.2 to 1.0 g/l, at the beginning of the seed culturing step.

3. The method of claim 2 wherein the total nitrogen content in the production medium is in the range from 0.3 to 0.6 g/l, at the beginning of the seed culturing step.

4. The method of claim 1 wherein the soluble nitrogen source is selected from the group consisting of ammonium nitrate, ammonium bromate, ammonium lactate, ammonium hydrochloride, ammonium phosphate, ammonium acetate, ammonium sulfate and urea.

5. The method of claim 1 wherein the water-insoluble nitrogen source is selected from the group consisting of soybean meal, peanut meal, corn extract and cotton seed extract.

* * * * *